United States Patent
Giese et al.

(10) Patent No.: US 12,239,477 B2
(45) Date of Patent: Mar. 4, 2025

(54) AUTOMATIC DETERMINATION OF A MOTION PARAMETER OF THE HEART

(71) Applicant: Siemens Healthineers AG, Forchheim (DE)

(72) Inventors: Daniel Giese, Erlangen (DE); Jens Wetzl, Spardorf (DE); Maria Monzon, Bilbao (ES); Carola Fischer, Nuremberg (DE); Seung Su Yoon, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 293 days.

(21) Appl. No.: 17/728,328

(22) Filed: Apr. 25, 2022

(65) Prior Publication Data
US 2022/0338829 A1    Oct. 27, 2022

(30) Foreign Application Priority Data
Apr. 27, 2021  (EP) .................................. 21170677

(51) Int. Cl.
*A61B 6/50*    (2024.01)
*A61B 6/00*    (2006.01)
(Continued)

(52) U.S. Cl.
CPC ............ *A61B 6/503* (2013.01); *A61B 6/5205* (2013.01); *G01R 33/5608* (2013.01);
(Continued)

(58) Field of Classification Search
CPC .. A61B 6/503; A61B 6/5205; G01R 33/5608; G06N 3/045; G06N 3/08
See application file for complete search history.

(56) References Cited

U.S. PATENT DOCUMENTS

2020/0219262 A1* 7/2020 Hsiao .................... G06V 10/764
2020/0380675 A1* 12/2020 Golden ................... G06T 7/143

FOREIGN PATENT DOCUMENTS

WO   WO-2020160664 A1 *  8/2020  ........... G06K 9/6257

OTHER PUBLICATIONS

Ronneberger et al., "U-Net: Convolutional Networks for Biomedical Image Segmentation"; Medical Image Computing and Computer-Assisted Intervention—MICCAI 2015 : 18th International Conference, Munich, Germany, Oct. 5-9, 2015; Oct. 9, 2015.
(Continued)

*Primary Examiner* — John R Wallace
(74) *Attorney, Agent, or Firm* — Banner & Witcoff Ltd.

(57) ABSTRACT

The disclosure relates to techniques for determining a motion parameter of a heart. A subset of a sequence of cardiac MR images is applied as a first input to a first trained convolutional neural network configured to determine, as a first output, a probability distribution of at least 2 anatomical landmarks. The sequence of cardiac MR images is cropped and realigned based on the at least 2 anatomical landmarks to determine a reframed and aligned sequence of new cardiac MR images showing the same orientation of the heart. The reframed and aligned sequence of new cardiac MR images is applied to a second trained convolutional neural network configured to determine, as a second output, a further probability distribution of the at least 2 anatomical landmarks in each new MR image of the reframed and aligned sequence, the motion parameter of the heart is determined based on the second output.

18 Claims, 16 Drawing Sheets

(51) Int. Cl.
    *G01R 33/56*    (2006.01)
    *G01R 33/563*   (2006.01)
    *G06N 3/045*    (2023.01)
    *G06N 3/08*     (2023.01)

(52) U.S. Cl.
    CPC ....... *G01R 33/56308* (2013.01); *G06N 3/045* (2023.01); *G06N 3/08* (2013.01)

(56) References Cited

OTHER PUBLICATIONS

Yuchi Han et al. "Cardiovascular Magnetic Resonance Characterization of Mitral Valve Prolapse", JACC: Cardiovascular Imagingvol. 1, No. 3, 2008.

Doesch C. et al., "Itral Annular Plane Systolic Excursion Is An Easy Tool For Fibrosis Detection By Lategadolinium Enhancement Cardiovascularmagnetic Resonance Imaging In Patients With Hypertrophic Cardiomyopathy", Archives of Cardiovascular Disease (2015) 108, 356-36.

Gonzales Ricardo A. et al., "Time-resolved tracking of the atrioventricular plane displacement in long-axis cine images with residual neural networks" in Proc. Intl. Soc. Mag. Reson. Med. 28 (2020), 2233.

Seemann F. et al., "Time-resolved tracking of the atrioventricular plane displacement in Cardiovascular Magnetic Resonance (CMR) images", BMC Med Imaging. 2017; 17: 19.

Seemann F. et al., "Valvular imaging in the era of feature?tracking: A slice?following cardiac MR sequence to measure mitral flow", vol. 51, Issue5, May 2020, pp. 1412-1421.

Ormiston J. et al., "Size and Motion of the Mitral Valve Annulus in Man", vol. 64, No. 1, 1081, Jul. 1981; http://ahajournals.org.

Bulluck H. et al., "A simple technique to measure TAPSE and MAPSE on CMR and normal values", Resonance 2014, 16(Suppl 1): P22.

Gütter C. et al., "Mitral valve annular velocity measurements derived from cine MRI: validation against Doppler echocardiography", J Cardiovasc Magn Resonv. 14(Suppl 1); 2012.

Cicek, Özgün et al., "3D U-Net: Learning Dense Volumetric Segmentation from Sparse Annotation"; 2016; arXiv:1606.06650; 2016.

Meng, Ye et al., "DeepTag: An Unsupervised Deep Learning Method for Motion Tracking on Cardiac Tagging Magnetic Resonance Images"; Arxiv Org, Cornell University Library, 201, Olin Library Cornell University Ithaca, NY 14853; Apr. 18, 2021 (Apr. 18, 2021), XP081930094.

Payer, Christian et al., "Multi-label Whole Heart Segmentation Using CNNs and Anatomical Label Configurations"; Mar. 15, 2018 (Mar. 15, 2018), ICIAP: International Conference on Image Analysis and Processing, 17th International Conference, Naples, Italy, Sep. 9-13, 2013. Proceedings; [Lecture Notes in Computer Science; Lect. Notes Computer], Springer, Berlin, Heidelberg; p. 190-1, XP047465749.

\* cited by examiner

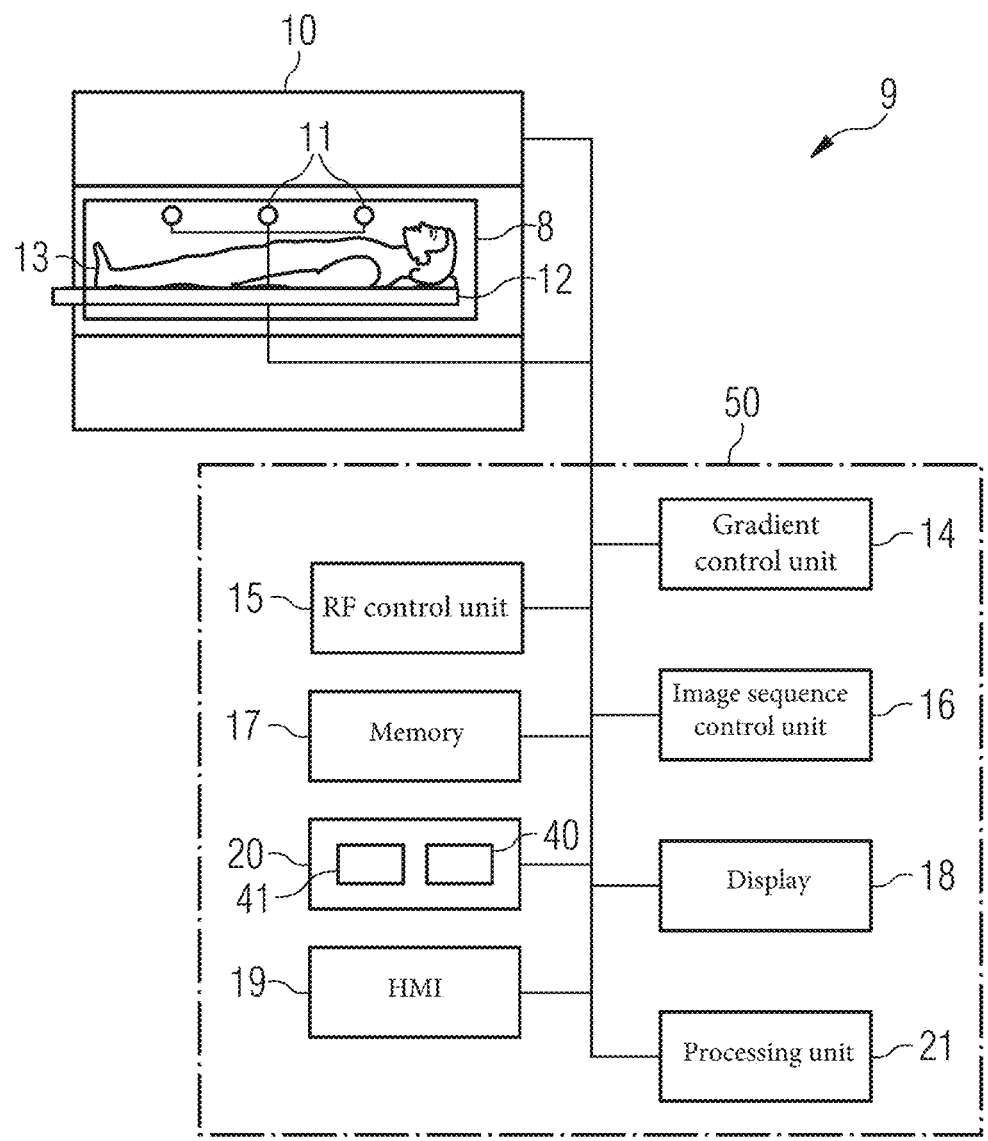

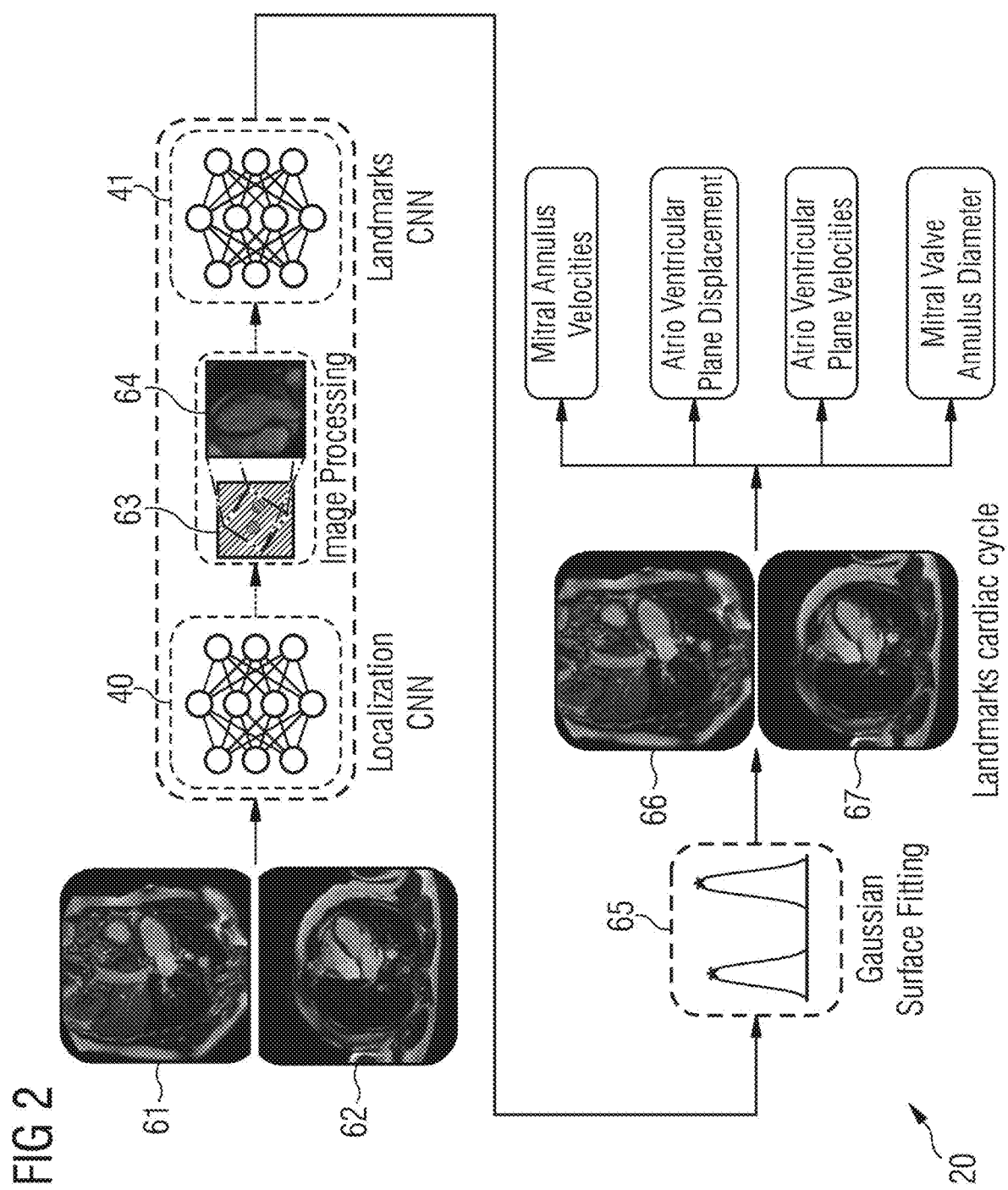

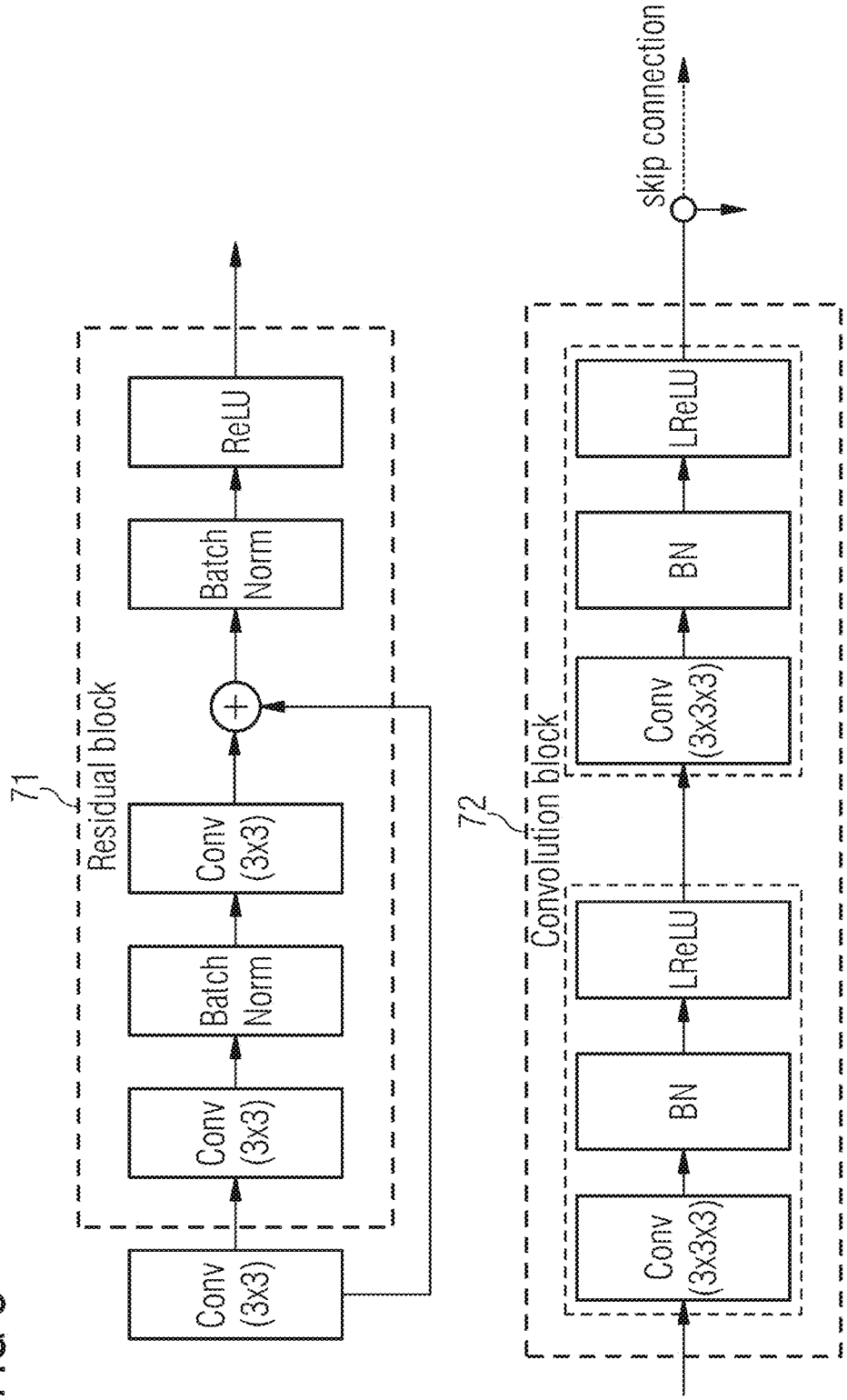

FIG 4

| FIG 4A |
|--------|
| FIG 4B |

FIG 4A

| Layers | Parameters | Stride | Feature maps out |
|---|---|---|---|
| Convolution block | k = 8 · (3x3) | S = (1x1), P = (1x1) | 8x128x128 |
| Residual Convolution block | k = 16 · (3x3) | S = (1x1), P = (1x1) | 16x128x128 |
| Max-pooling | F = (2x2) | S = (1x1) | 16x64x64 |
| Residual Convolution block | k = 24 · (3x3) | S = (1x1), P = (1x1) | 24x64x64 |
| Max-pooling | F = (2x2) | S = (1x1) | 24x32x32 |
| Dilated convolution block | (4x) k = 24 · (3x3) | S = (1x1), P = (1x1) | 24x32x32 |
| Transposed Conv block | 16 · k = (3x3) | S = (2x2), P = (1x1) | 24x64x64 |
| Concat and Residual Conv block | k = 24 · (3x3) | S = (1x1), P = (1x1) | 16x64x64 |
| Transposed Conv block | 8 · k = (3x3) | S = (2x2), P = (1x1) | 16x128x128 |
| Concat and Residual Conv block | k = 16 · (3x3) | S = (1x1), P = (1x1) | 8x128x128 |
| Output Convolution block | k = 3 · (3x3) | S = (1x1), P = (1x1) | 3x128x128 |

FIG 4B

| Layers | Parameters | Stride | Feature maps out |
|---|---|---|---|
| Convolution block | k = 32 · (3x3x3) | S = (1x1x1) | 32x32x256x256 |
| Max-pooling | F = (1x2x2) | S = (1x1) | 32x32x128x128 |
| Convolution block | k = 64 · (3x3x3) | S = (1x1x1) | 64x32x128x128 |
| Max-pooling | F = (1x2x2) | S = (1x1) | 64x32x64x64 |
| Convolution block | k = 128 · (3x3x3) | S = (1x1x1) | 128x32x64x64 |
| Max-pooling | F = (2x2x2) | S = (1x1x1) | 128x16x32x32 |
| Convolutional block | k = 256 · (3x3x3) | S = (1x1x1) | 256x16x32x32 |
| Max-pooling | F = (2x2x2) | S = (1x1x1) | 256x8x16x16 |
| Bottleneck convolution | k = 512 · (3x3x3) | S = (1x1x1) | 512x8x16x16 |
| Transpose Conv block | k = 512 · (1x1x1) | S = (2x2x2) | 512x16x32x32 |
| Concat and Convolution | k = 768 · (3x3x3) | S = (1x1x1) | 256x16x32x32 |
| Transpose Conv Block | k = 256 · (1x1x1) | S = (2x2x2) | 256x32x64x64 |
| Concat and Convolution | k = 384 · (3x3x3) | S = (1x1x1) | 128x32x64x64 |
| Transpose Conv Block | k = 128 · (3x3x3) | S = (1x2x2) | 128x32x128x128 |
| Concat and Convolution | k = 192 · (3x3x3) | S = (1x1x1) | 62x32x128x128 |
| Transpose Conv Block | k = 64 · (3x3x3) | S = (1x2x2) | 64x32x256x256 |
| Concat and Convolution | k = 96 · (3x3x3) | S = (1x1x1) | 32x32x256x256 |
| Output Convolution block | k = 2 · (3x3x3) | S = (1x1x1) | 2x32x256x256 |
| Soft arg-max activation | 2x32x256x256 | - | 2x32x2 |

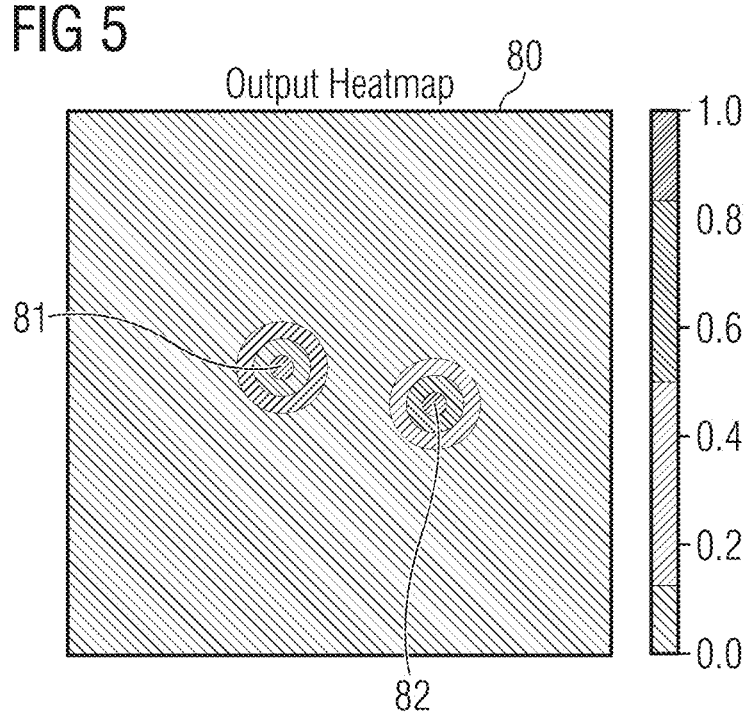

FIG 6
FIG 6A
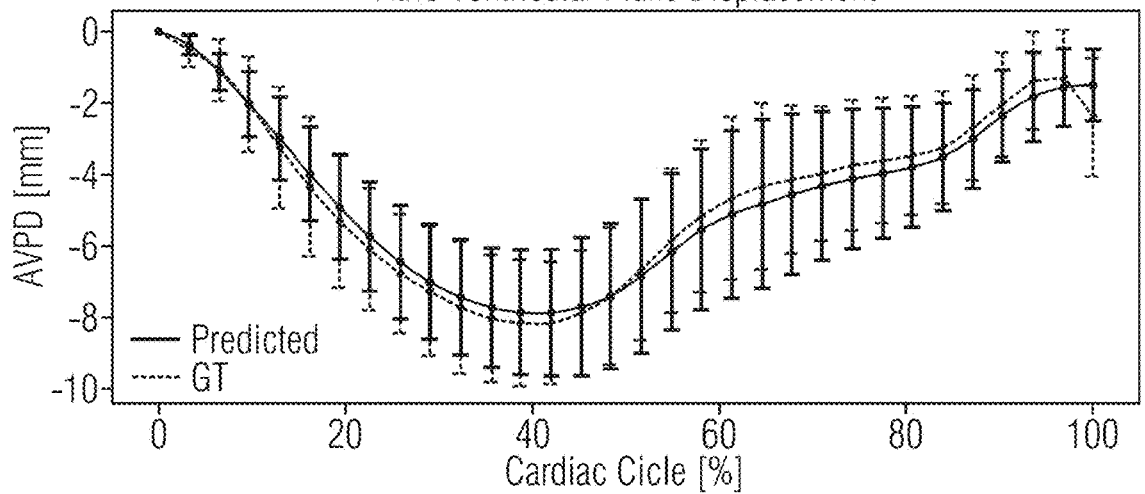
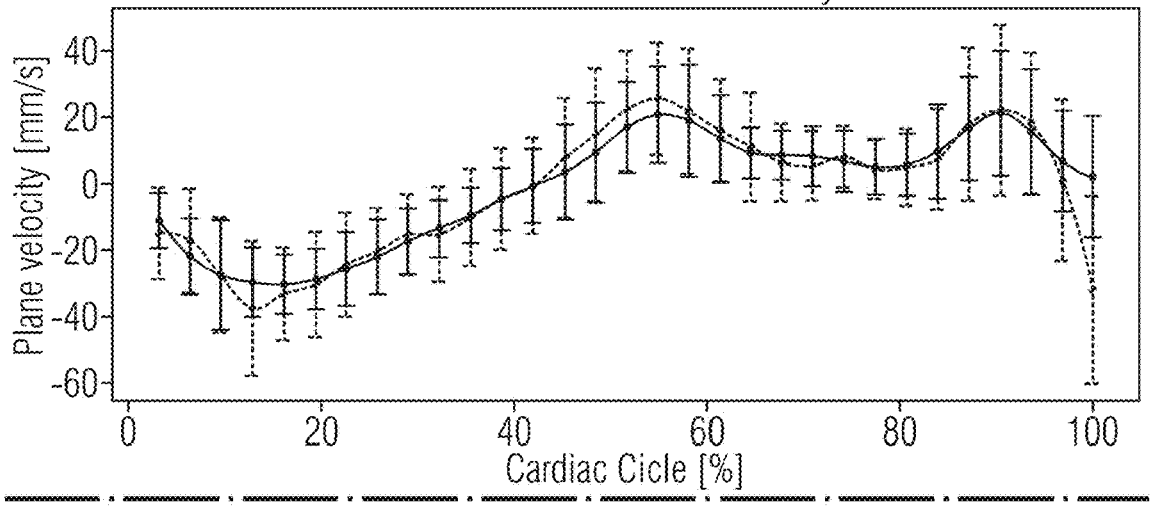

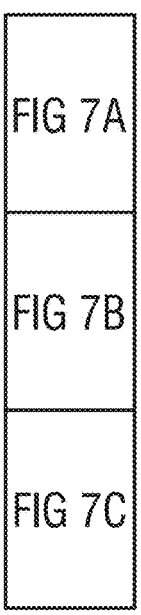
FIG 7
FIG 7A
FIG 7B
FIG 7C
FIG 7A
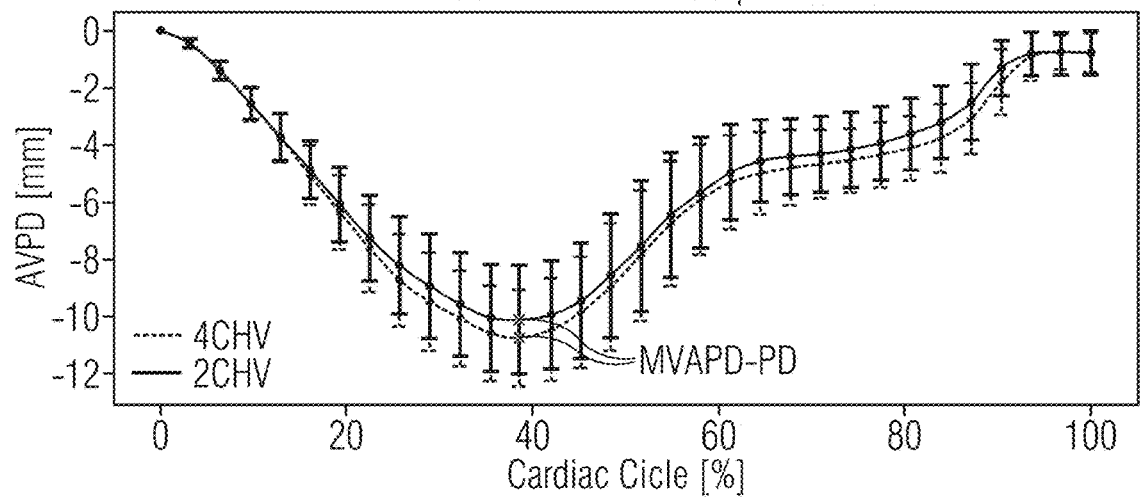
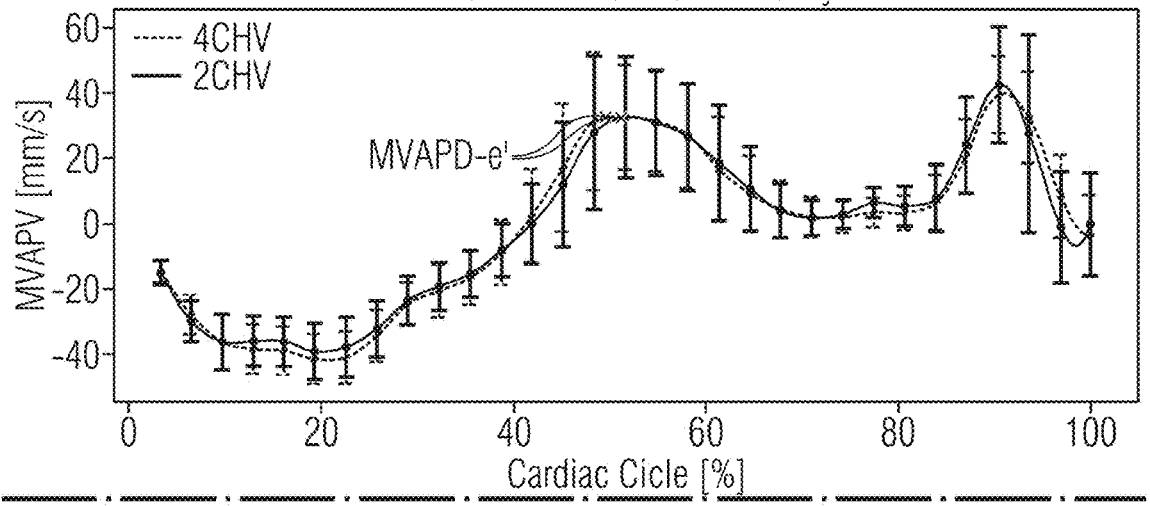

FIG 8B
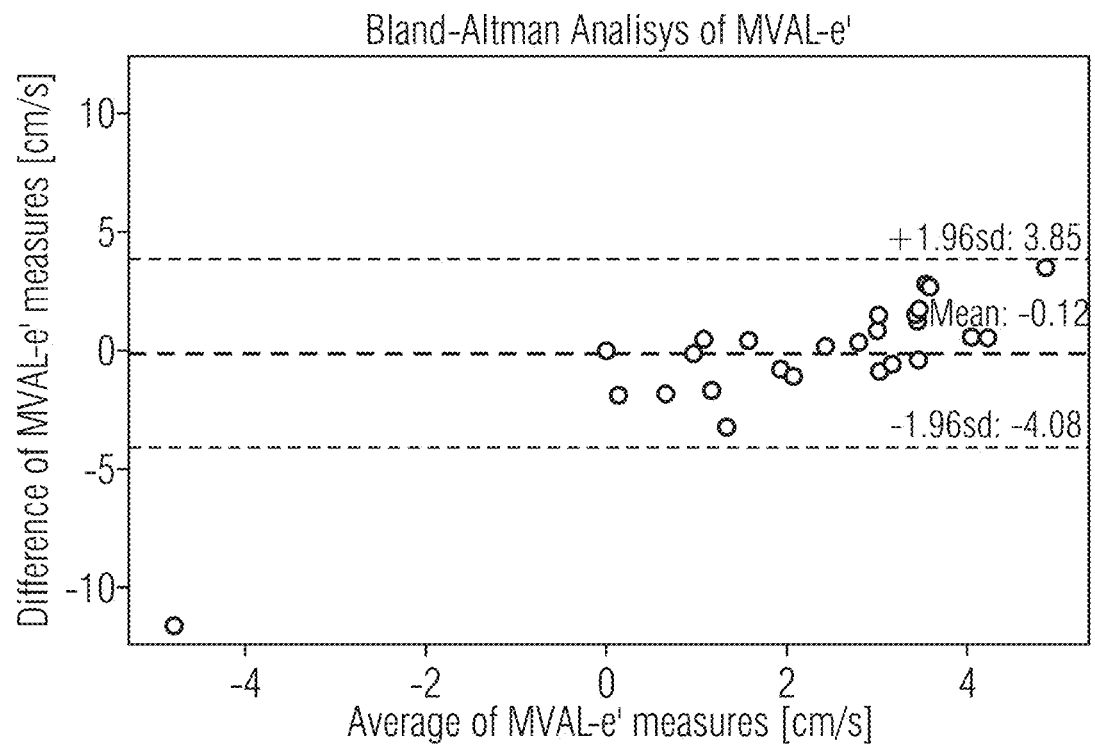
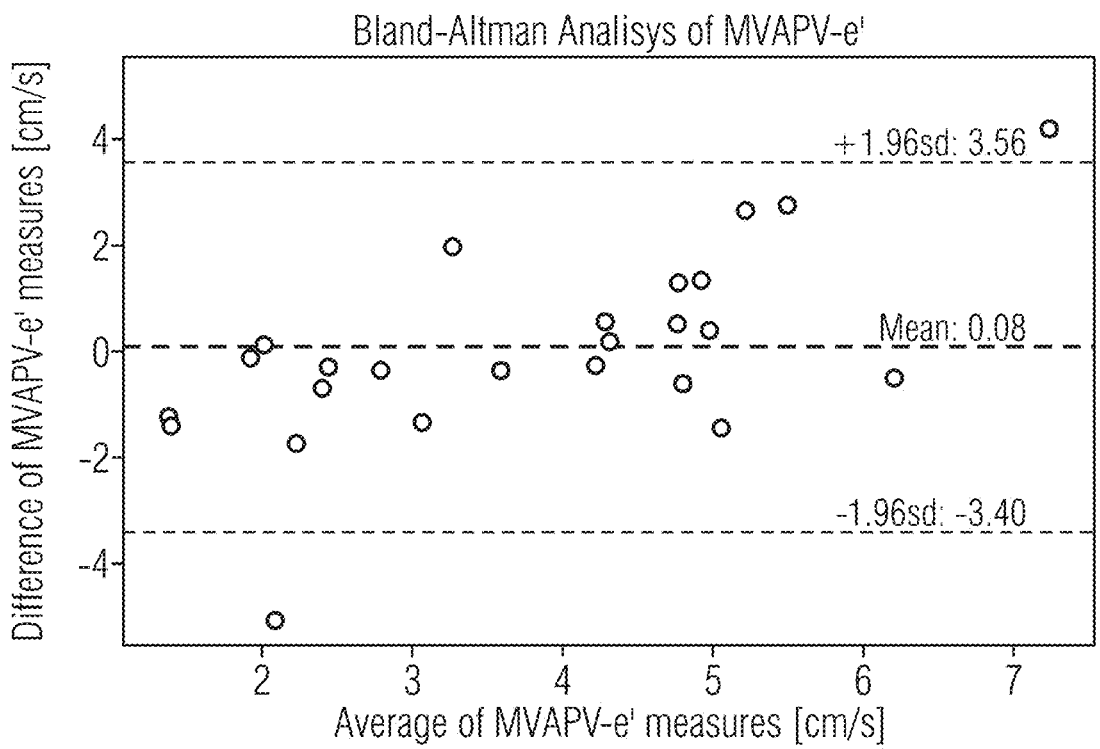

FIG 8C
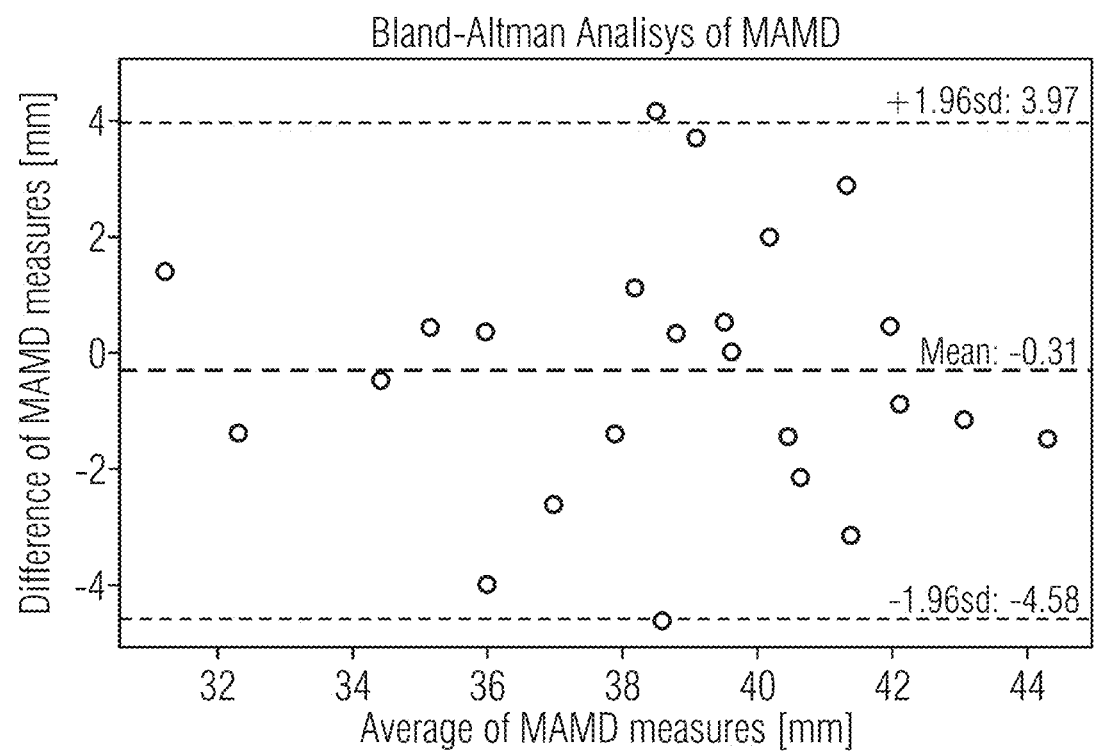
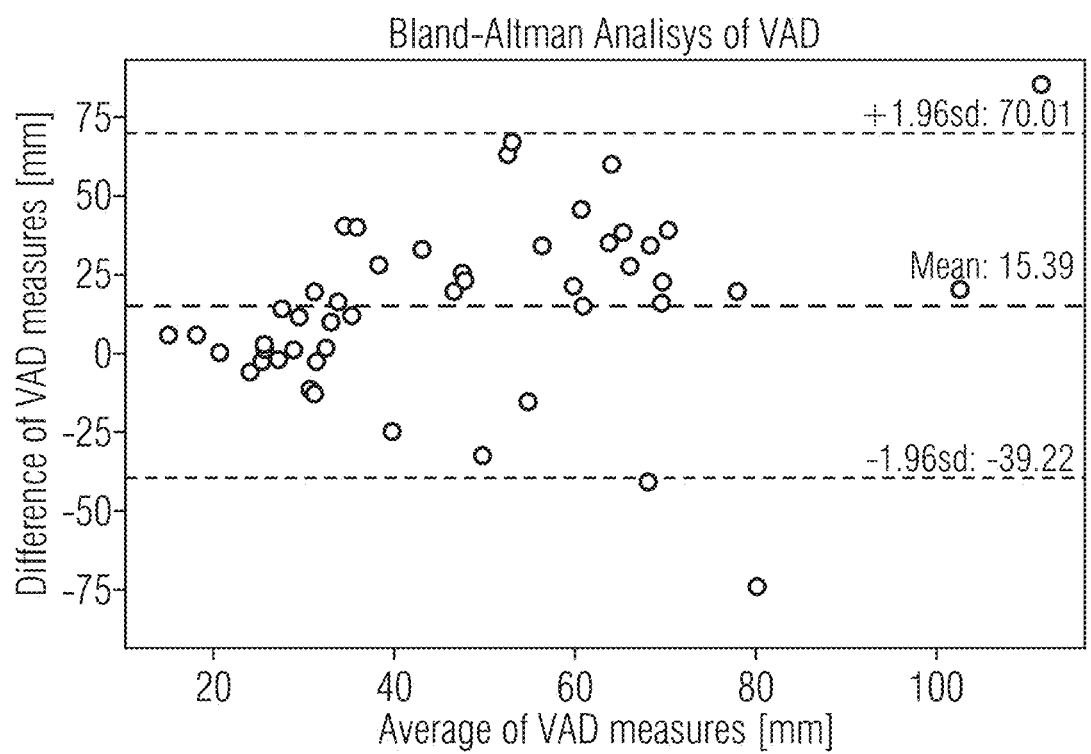

AUTOMATIC DETERMINATION OF A MOTION PARAMETER OF THE HEART

CROSS-REFERENCE TO RELATED APPLICATIONS

The present application claims the benefit of the filing date of European patent application no. EP 21170677.5, filed on Apr. 27, 2021, the contents of which are incorporated herein by reference in their entirety.

TECHNICAL FIELD

The disclosure relates to a method for determining a motion parameter of the heart, a corresponding entity configured to determine the motion parameter, a computer program comprising program code, and a carrier comprising the computer program.

BACKGROUND

Overall prevalence of heart failure with preserved ejection fraction (HFpEF) has been known to be 1.1-5.5% in the general population and is typically related to diastolic dysfunction. It is further known that the analysis of the mitral valve annulus (MVA) throughout the cardiac cycle might act, amongst others, as a predictor for HFpEF.

Currently, the diagnosis of heart failure, especially with preserved ejection fraction, remains extremely challenging due to the complexity of the disease and its early subtle effects on the motion of the heart and the mitral valve, especially. The interplay between motion and flow remains unsatisfactorily understood. It is possible to extract motion related parameters of the heart from echo-doppler acquisitions and/or MR images. These approaches are, however, time-consuming and do not provide satisfactory results.

Accordingly, a need exists to improve the determination of motion parameters of the heart.

SUMMARY

This need is met by the features of the aspects as discussed herein, including the claims.

According to a first aspect, a method for determining a motion parameter of the heart is provided, wherein the method comprises the step of determining a sequence of cardiac MR images showing a time resolved motion of the heart. Furthermore, a subset of the sequence of cardiac MR images is applied as a first input to a first trained convolutional neural network, which is configured to determine, as a first output, a probability distribution of at least two anatomical landmarks in the subset. The sequence of cardiac MR images is cropped and aligned based on the at least two anatomical landmarks to determine a reframed and aligned sequence of new cardiac MR images, wherein all the new images of the reframed and aligned sequence show the same orientation of the heart. The reframed and aligned sequence of new cardiac MR images is applied to a second trained convolutional neural network, which is configured to determine, as a second output, a further probability distribution of the at least two anatomical landmarks in each new MR image of the reframed and aligned sequence. Finally, the motion parameter of the heart is determined based on the second output.

The proposed method provides a robust and fully-automated algorithm for the detection of the motion parameter. The first trained convolutional neural network is configured to identify regions of interest including the two anatomical landmarks such as the mitral valve, wherein the second trained convolutional neural network extracts the landmark in the time resolved images of the heart using the identified regions of interest. The movement of the landmark can then be used to determine the required motion parameters.

Furthermore, a corresponding entity is provided that is configured to determine the motion parameter, wherein the entity comprises a memory and at least one processing unit which is configured to operate as discussed above or as discussed in further detail below.

Furthermore, a computer program comprising program code to be executed by at least one processing unit of the entity is provided, wherein the execution of the program code causes the at least one processing unit to carry out a method as discussed above or as discussed in further detail below.

Additionally, a carrier comprising the computer program is provided, wherein the carrier may include an electronic signal, an optical signal, a radio signal, a (e.g. non-transitory) computer-readable storage medium, etc.

It is to be understood that the features mentioned above and features yet to be explained below can be used not only in the respective combinations indicated, but also in other combinations, or in isolation without departing from the scope of the disclosure.

Features of the above-mentioned aspects and embodiments described below may be combined with each other in other embodiments unless explicitly mentioned otherwise.

BRIEF DESCRIPTION OF THE DRAWINGS/FIGURES

The foregoing and additional features and effects of the disclosure will become apparent from the following detailed description when read in conjunction with the accompanying drawings in which like reference numerals refer to like elements:

FIG. 1 shows an example schematic view of an MR imaging system configured to determine a motion related parameter of the heart, in accordance with one of or more aspects of the present disclosure.

FIG. 2 shows an example schematic view of an entity or a system configured to determine the motion parameter using two convolutional neural networks, in accordance with one of or more aspects of the present disclosure.

FIG. 3 shows example feature extraction convolution blocks used in the neural networks of FIG. 2, in accordance with one of or more aspects of the present disclosure.

FIGS. 4a and 4b show an example detailed view of the composition of the two neural networks, in accordance with one of or more aspects of the present disclosure.

FIG. 5 shows an example output generated by the two neural networks indicating a heat map or likelihood distribution of the identified landmarks, in accordance with one of or more aspects of the present disclosure.

FIG. 6a to 6c show examples of derived motion parameters compared to the ground truth data, in accordance with one of or more aspects of the present disclosure.

FIG. 7a to 7c show an example application of the system of FIG. 2 for unlabeled image data sets, in accordance with one of or more aspects of the present disclosure.

DETAILED DESCRIPTION

Figure 6B:
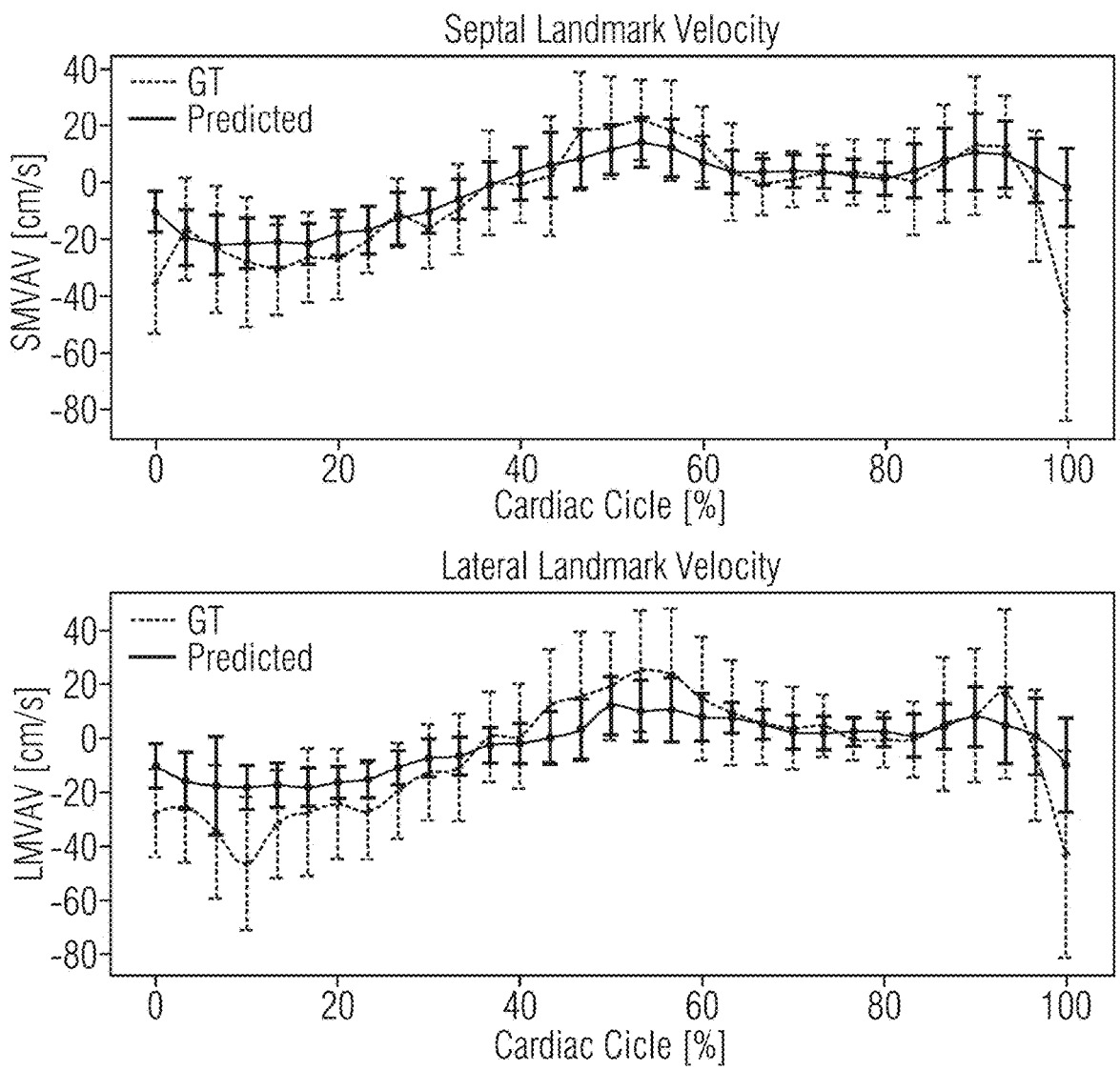

In the following, embodiments of the disclosure will be described in detail with reference to the accompanying drawings. It is to be understood that the following description of embodiments is not to be taken in a limiting sense. The scope of the disclosure is not intended to be limited by the embodiments described hereinafter or by the drawings, which are to be illustrative only.

The drawings are to be regarded as being schematic representations and elements illustrated in the drawings are not necessarily shown to scale. Rather, the various elements are represented such, that their function in general purpose becomes apparent to a person with skill in the art. Any connection or coupling between functional blocks, devices, components of physical or functional units shown in the drawings and described hereinafter may be implemented by an indirect or direct connection. A coupling between components may be established over a wired or wireless connection. Functional blocks may be implemented in hardware, software, firmware, or a combination thereof.

In the following, a fully automated algorithm for detecting the mitral valve annulus is disclosed. However, this is by way of example and not limitation, and it should be understood that any other valve of the heart may be used. The MR images can be a 2 chamber (2CHV), and/or 4 chamber (4CHV) MR images such as CMR (Cardiac Magnetic Resonance) images. The system discussed herein initially detects the mitral valve region of interest before extracting the time resolved landmarks of the mitral valve annulus. This information is then used to extract the motion related parameters including displacements, velocities, and diameters. The system performance is analyzed based on pre-annotated data sets, which were annotated by experts marking the desired region of interests. Thereafter, the motion parameters were extracted retrospectively on N=1468 unlabeled data sets. The system may automatically calculate motion related parameters such as the mitral valve velocities, mitral valve plane motion, mitral valve diameters and how these parameters evolve over time during the heartbeat. These parameters have shown to be clinically important for the automatic assessment of heart failure, especially for heart failure with preserved ejection fraction which is typically related to diastolic dysfunction.

FIG. 1 shows an example schematic view of an MR imaging system 9, which comprises a magnet 10 generating the magnetic field B0. The patient or object under examination 13 lying on a table 12 is moved into the center of the MR imaging system 9, where the MR signals can be detected after excitation by RF pulses using coils 11. By applying RF pulses and magnetic field gradients, the nuclear spins of object 13, especially the parts located in the receiving coils, are excited and location coded currents induced by relaxation can be detected. The way how MR images, especially CINE images, are generated and how the MR signals are detected using a sequence of RF pulses and a sequence of magnetic field gradients is known, and thus a detailed explanation thereof is omitted. The MR system may further comprise shim coils 8 which are used to correct in-homogeneities of the magnetic field B0.

The MR imaging system 9 comprises a control module 50 (e.g. a controller or control circuitry) which is used for controlling the MR imaging system. The control module 50 comprises a gradient control unit 14 for controlling and switching the magnetic field gradients, an RF control unit 15 for controlling and generating RF pulses for the imaging sequences. The image sequence control unit 16 is provided to control the sequence of the applied RF pulses and magnetic field gradients and thus is also configured to partly control the gradient control unit 14 and the RF control unit 15. In a memory 17, computer programs needed for operating the MR imaging system and the imaging sequences necessary for generating the MR images can be stored together with the generated MR images. The MR images and any further information can be displayed on a display 18 wherein a human machine interface 19 is provided, which can be used by an operator of the MR imaging system to control the MR imaging system. Furthermore a machine learning module 20 is provided which comprises a first trained neural network 40 and a second trained neural network 41. The machine learning module with the two convolutional neural networks 40 and 41 is configured, as will be explained below to generate and output a likelihood distribution of certain anatomical landmarks of the heart such as the mitral valve annulus. A central processing unit 21 can coordinate the operation of the different functional units shown in FIG. 1, and can comprise one or more processors, which can carry out (i.e. execute) the instructions stored on the memory 17. The memory can include program code to be executed by the processing unit 21.

FIG. 2 shows a schematic view of module or device 20 which is configured to automatically determine heart related parameters such as valve velocities, displacements, or diameters. The device 20 may form part of the control module 50 as shown in FIG. 1 or be implemented as a separate device. In any event, the device 20 may represent any suitable combination of processors, hardware, software, etc., to realize the functions of the convolutional neural networks 40, 41 as discussed herein.

The MR system 9 generates a time series of MR images of the heart, by way of example a two-chamber, 2 CHV, or a four-chamber view, 4 CHV, the two image options being schematically shown as image 61 and 62 in FIG. 2. For each of the images a time series of images is present, e.g. a sequence of cardiac MR images. The first trained neural network 40 is a convolutional neural network and is configured to detect the landmark such as the mitral valve. The network 40 can be a 2D network in which a single image is input such as the first image of the time series of MR images. The output of the first neural network 40 is a heat map, such as the heat map 63 shown in FIG. 2, in which the two landmarks, the mitral valves, are shown. Based on the two landmarks, the image size is adjusted by cropping the image (e.g. to generate a square image size) as shown and the image is rotated so that all images of the time series now have the same orientation, here the apex of the heart is oriented in the upward direction. Accordingly, the first image in the series is passed through the first neural network 40 to determine a more detailed view of the region of interest and to provide a defined orientation for all of the images of the time series.

It is possible to interpolate the sequence of cardiac MR images, such as 32 time frames, so that the same number of MR images is present, and can be used as input for the second network 41. Both networks are chained convolutional neural networks, and are both trained to detect landmarks based on a heat map regression task. The first network can be a residual 2D Unet as described inter alia in Ronneberger, Olaf, et al. U-net: Convolutional networks for biomedical image segmentation. International Conference on Medical image computing and computer-assisted intervention. Springer, Cham, 2015. The network identifies the mitral valve annulus in both the four-chamber view and/or the two-chamber view by regressing three landmarks on the first timeframe of each series. The third landmark can be the apex of the heart. After rotation as shown by the image 63 and after cropping and a pixel space interpolation, a series of reframed and aligned images is generated such as image 64. These images are input into the second neural network a 3D UNet e.g. Özgün Çiçek, et. al. 3D U-Net: Learning Dense Volumetric Segmentation from Sparse Annotation. CoRR abs/1606.06650 (2016), wherein the second network extracts the time resolved heat maps of both landmarks.

A postprocessing step as shown in image 65 fits a defined distribution such as a Gaussian distribution to refine the final landmark coordinates.

The result is a time series of images 66 or 67, in which the landmark such as the mitral valve annulus is indicated and marked. Based on the evolution of the landmarks, it is possible to determine different motion parameters such as the mitral annulus velocities, the atrioventricular plane displacement, the atrioventricular plane velocities, or the mitral valve annulus diameter. Accordingly, it is possible to determine clinically-relevant parameters of interest such as the mitral annulus tissue velocity, the time resolved atrioventricular plane displacement and peak displacement, or slice tracking of image slices based on atrioventricular plane displacement. Furthermore, it is possible to determine the time resolved atrioventricular plane velocity curves and early diastolic velocity, an indication for the systolic or diastolic function. Further parameters such as the end systolic long axis mitral annular diameter can be determined or the mitral annular total motion quantification, such as the accumulation over the cardiac cycle of the displacement for every landmark in millimeters. Furthermore, it is possible to determine the maximum minus the minimum displacement, such as the distance traveled by the lateral annulus from the end diastole to the end systole. Furthermore, it is possible to determine the mitral valve contraction, e.g. in mm such as the diameter contraction defining the time resolved difference between the maximum and the minimum diameter.

In the following training of the data used to train network 40 and 41 is discussed in more detail.

Ground truths annotated images from 83 subjects were provided, which were generated at 1.5 and 3 Tesla, wherein the images show two-chamber views and four-chamber views. The data included semi-automatically annotated landmarks showing the mitral valve annulus, MVA throughout the cardiac cycle. The mean in-plane resolution was 1.48±0.35 mm.

Training: The model was trained from scratch using the Adaptive Wing Loss on the heatmaps while decreasing the heatmaps standard deviation exponentially throughout training epochs $\sigma_{ep}=16\cdot 0.95^{ep}$. The networks were trained using Adam optimizer with momentum of $\beta=0.9$ and learning rate $\lambda=0.0001$ with weight decay regularization. Online data augmentation was performed using random rotation, contrast enhancement, translation, maximum clipping, blurring, and noise addition.

FIG. 3 shows a more detailed view of the feature extraction convolutional blocks. FIG. 3 shows the residual blocks 71 corresponding to the first neural network and the convolution blocks 72 corresponding to the second neural network. The blocks contain convolutions, batch normalizations, as well as activation functions such as the rectified linear unit (ReLU) or variants thereof. 40 and 41 further illustrate the typical residual block addition and skip connections, respectively.

FIG. 4a shows a more detailed view of the first neural network 40, and FIG. 4b shows the second neural network 41 comprising the layer composition. The networks 40 and 41 comprise feature extraction 2D residual and 3D convolutional blocks. Each residual block comprises a spatial convolution (CONV) 3×3, batch normalization, BN, and Leaky Rectified Linear Units, LReLU, activation layers. The 3D block comprises double spatial and temporal CONV (3*3*3)-BN-LReLU operations. The architecture of Network 40 is based on the 2D Unet with 3 encoder-decoder blocks. In network 41, for down sampling asymmetrical max-pooling layers were applied into temporal and spatial dimensions.

FIG. 5 shows a schematic view of a heat map or probability distribution as generated by the two networks. In the heat map or probability distribution 80, two landmarks such as the landmarks 81 and 82 are generated.

Figure 6C:
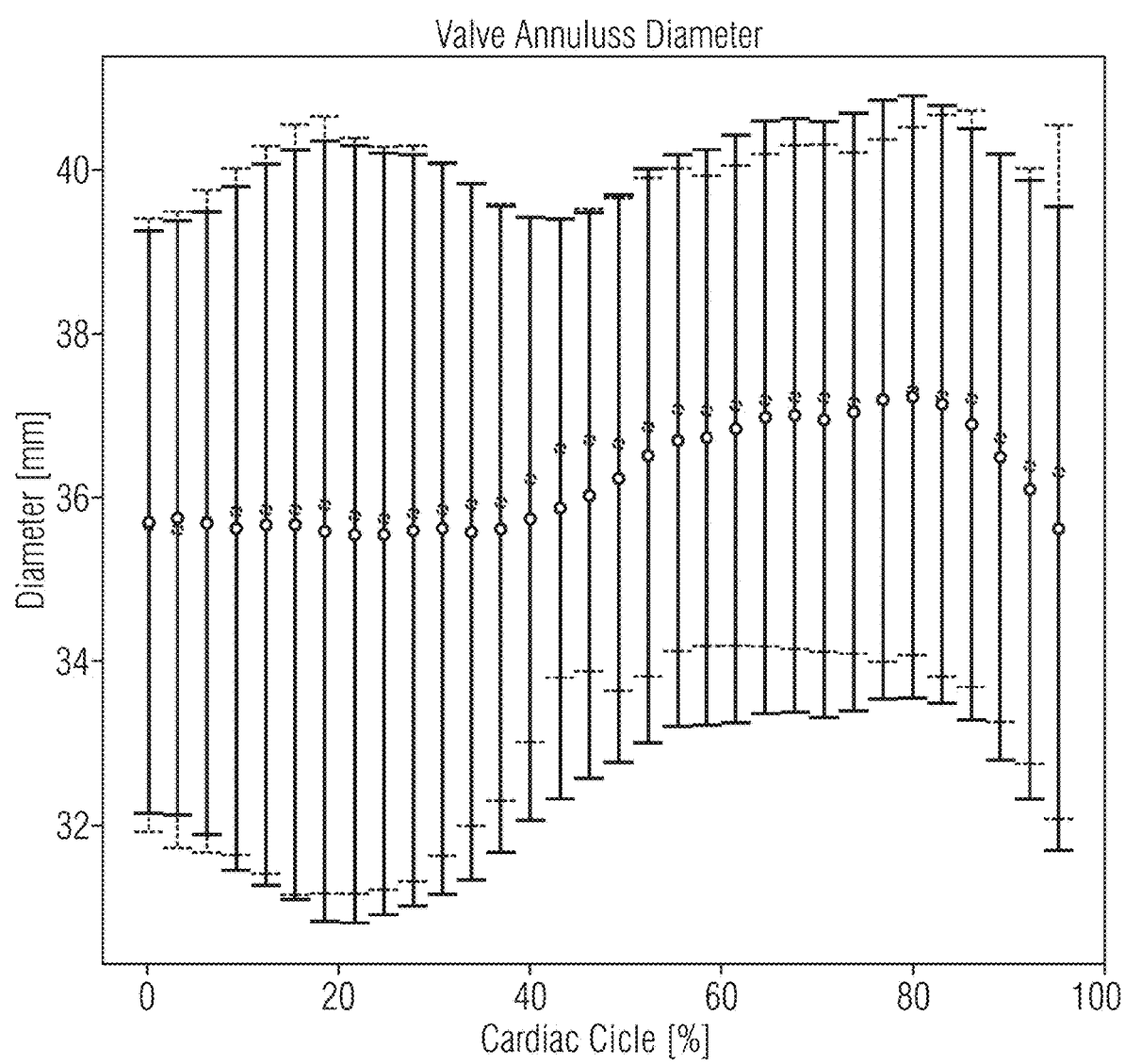

In FIG. 6a to 6c, the different extracted parameters are shown as predicted by the networks (predicted curve) versus the ground truth data (GT), wherein the time resolved motion curves are extracted from the neural networks and the following parameters are calculated:

MVA plane displacement (MVAPD) curve was defined as the time-resolved perpendicular distance of the MVA plane relative to the first frame, Peak displacement (MVAPD-PD) was also extracted.

MVA plane velocity (MVAPV) was derived as the MVAPD time-resolved discrete temporal derivate. Early diastolic velocity (MVAPV-e') was then defined as the central maximum of the MVAPV.

The total motion of the annulus (VAD) was quantified as the total displacement sum over all timeframes in mm The septal and lateral MVA landmark velocity curves (SMVAV, LMVAV) were computed as the temporal derivative of each landmark displacement. The central maximum of each curve represents early annular diastolic velocity (MAVL-e').

The time-resolved diameter evolution throughout the cardiac cycle was derived as the Euclidean distance between landmarks in mm, and the maximum diameter (MAMD), as well as the difference between maximum and minimum diameter (MACD), were extracted.

Analysis: Network accuracy was evaluated by the root mean square difference between ground truth and detected landmarks as well as by a Bland-Altmann analysis (FIG. 8a to 8d) on extracted motion parameters. On 1468 unlabeled datasets acquired on 1.5 T systems, successful inference was assessed by detecting unambiguous outliers. Every tracked series whose plane displacement is not temporally smooth (mean standard deviation) at any cardiac phase is discarded. Finally, motion parameters were extracted from this data (FIG. 7a to 7c).

One of the curves shows the ground truth data, wherein the other curve shows the output result as calculated based on the output from the neural networks.

Figure 7B:
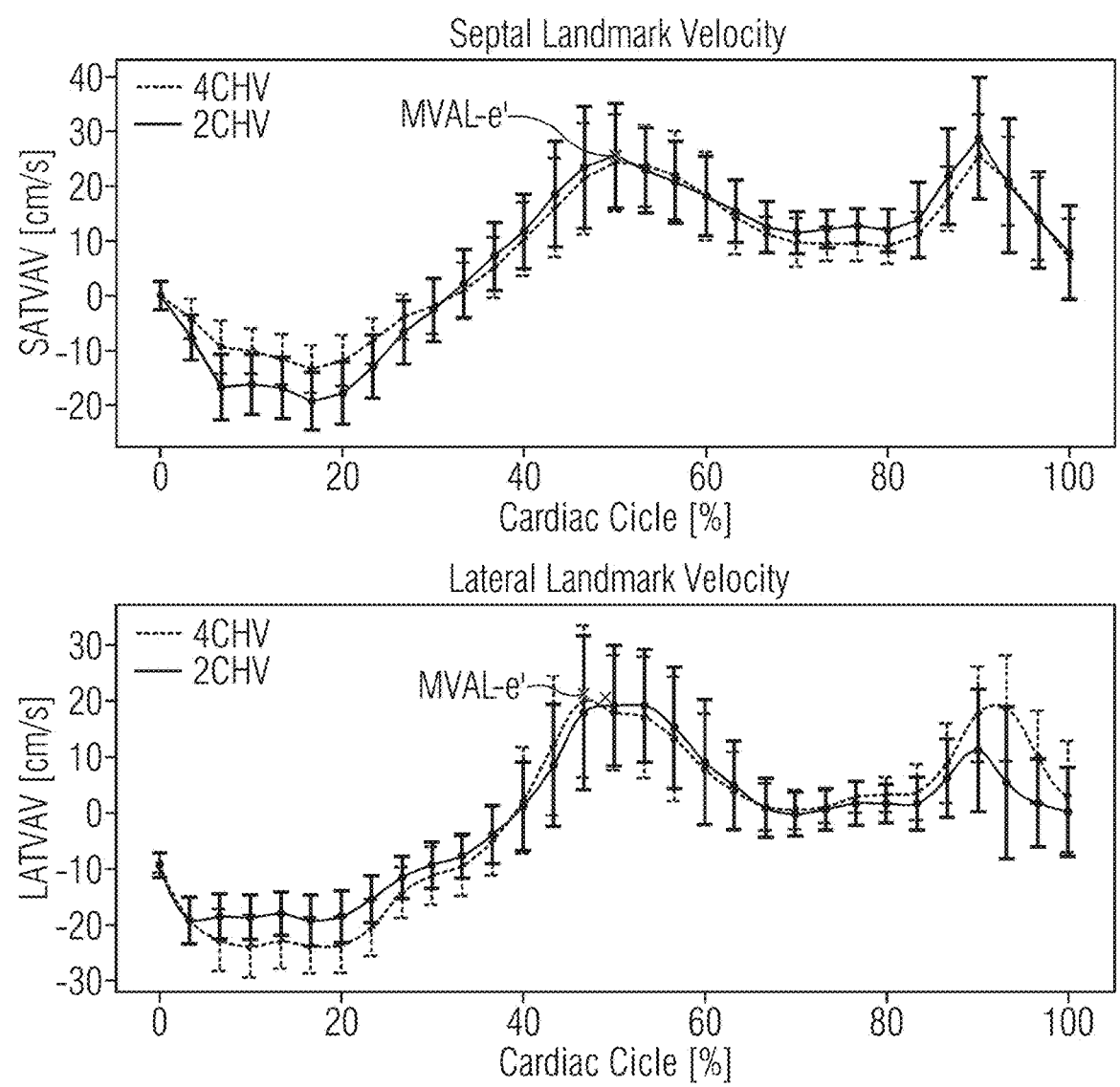
Figure 7C:
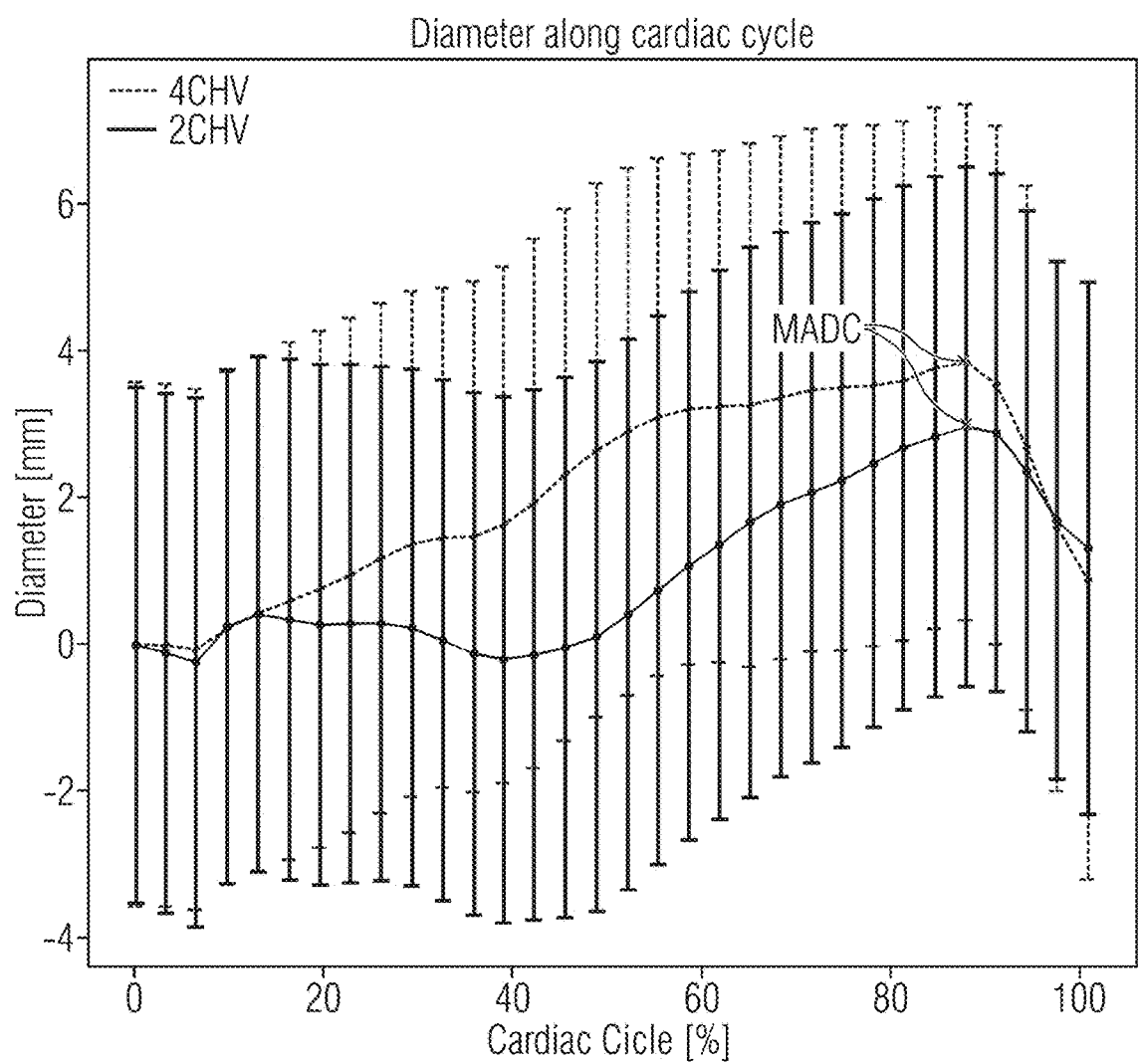

Furthermore, the 2 networks were used for unlabeled images as shown in FIG. 7, wherein FIGS. 7a to c show extracted parameters from 1468 unlabeled data sets in which data are shown for the two and four-chamber view respectively. The bars represent the standard deviation over datasets in each plot.

Figure 8:
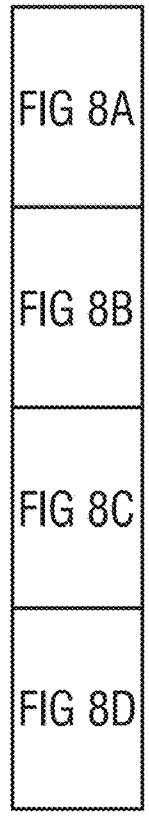
FIG. 8a to 8d show an example Bland-Altmann analysis of the data output by the system including the two neural networks, in accordance with one of or more aspects of the present disclosure.
Figure 8A:
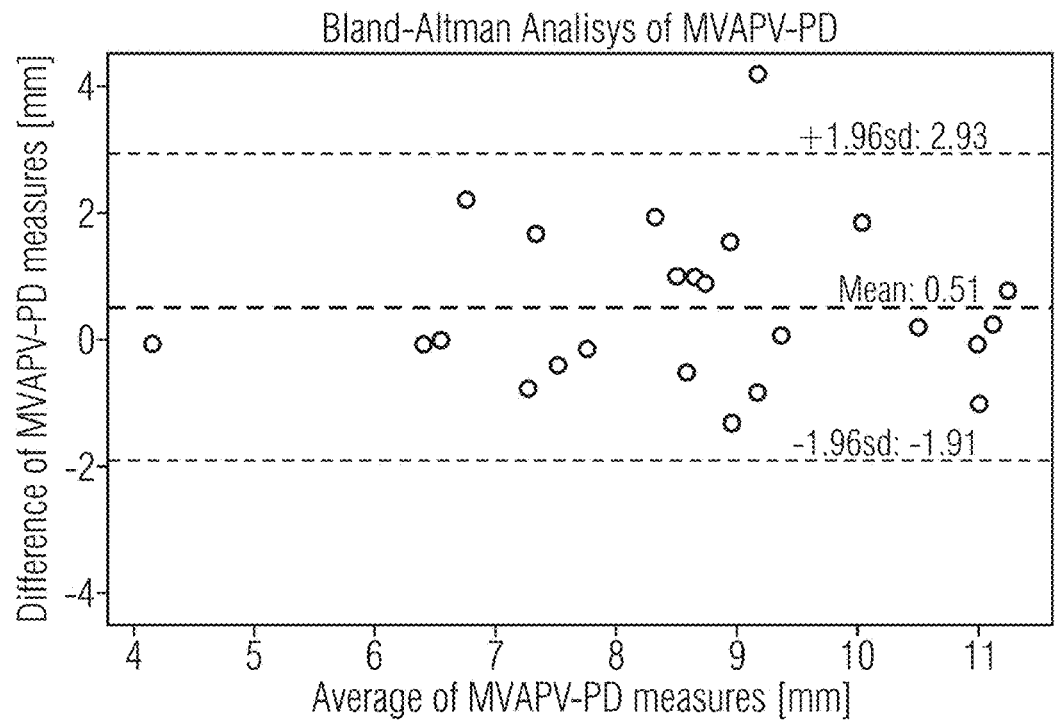
Figure 8D:
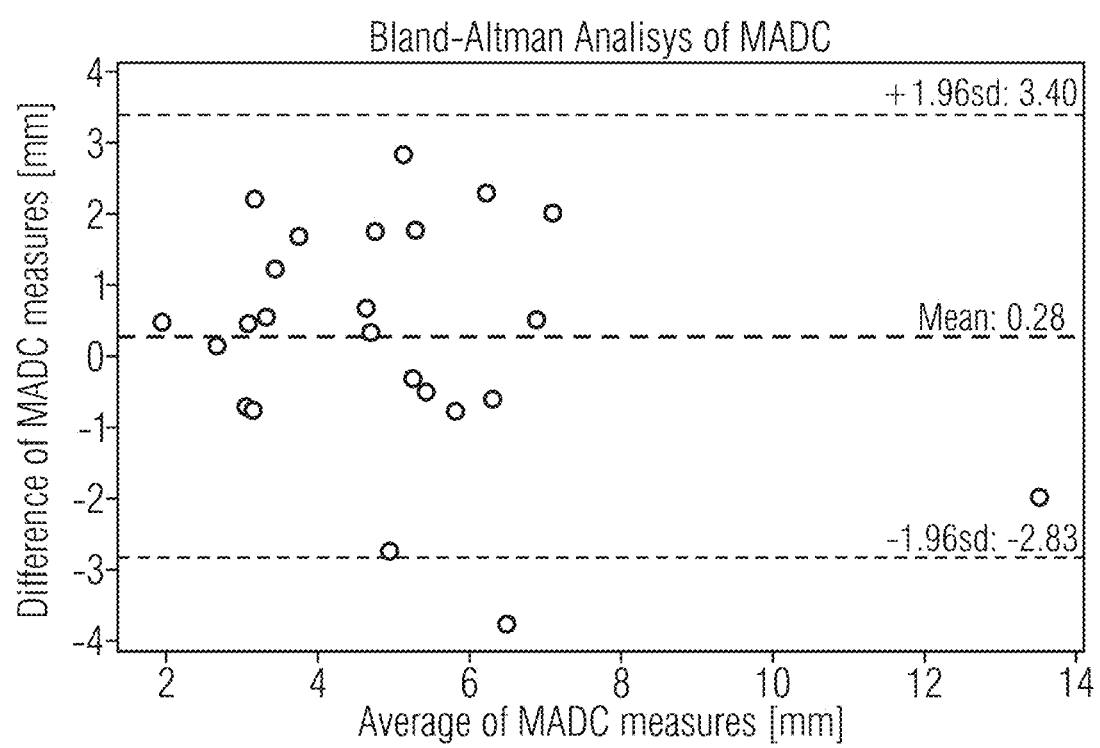

FIG. 8 shows a Bland-Altmann analysis. Landmark coordinate mean errors of 1.75±0.64 mm (2CHV) and 1.74±0.72 mm (4CHV) were achieved as compared to ground truth, manually annotated datasets.

The Bland-Altmann analysis of FIG. 8 revealed the following mean agreement values: MVAPD-PD: 0.53±2.442 mm, MVAPV-e': 0.53±3.48 cm/s, VAD: 15.39 0177 54.62 mm, MAVL-e': 0.12±3.73 cm/s, MAMD: 0.31±3.66 mm, MADC: 0.28±3.12 mm The localization network fails to locate the ROI in less than 0.5% of unlabeled datasets and at least one time-frame was not smoothly tracked in 16.53%.

From the above, some general conclusions can be drawn.

First of all, a sequence of cardiac MR images is determined which shows the time resolved motion of the heart. Then, a subset of images is applied to the first trained convolutional neural network 40. The subset of the sequence of cardiac MR images can comprise a single MR image of the sequence of cardiac MR images, e.g. a first timeframe in the sequence of cardiac MR images, and the first trained convolutional neural network is a 2D convolutional neural network.

As one example, the second trained convolutional neural network is a 3D network, which is able to process the time series of MR images.

Different motion parameters can be determined based on the identified landmarks, such as the plane displacement of the mitral valve annulus, the plane velocity of the mitral valve annulus, the total motion of the annulus, the septal or lateral velocity of the mitral valve annulus, the evolution of the diameter of the mitral valve annulus, a mitral annular tissue velocity, a time resolved atrioventricular plane velocity, or the end systolic long axis mitral annular diameter.

Furthermore, a pixel space interpolation is applied to the images before the reframed and aligned sequence is applied to the second trained convolutional neural network.

Furthermore, it is possible to carry out a fitting, for each of the at least two landmarks in which a defined probability distribution such as Gaussian distribution is fitted to the further probability distribution as output by the second network, wherein the maximum of the fitted distribution is used as the final position of the at least two landmarks, which is used to determine the motion parameter.

The method may be repeated with two sequences of MR images having different slice orientations, so that at least four anatomical landmarks are obtained and the motion parameter is determined based on the at least four anatomical landmarks. By way of example, when the image plane is rotated by 90°, four different landmarks on the annulus may be obtained.

The two convolutional neural networks 40 and 41 may be both trained with the same training data in which the at least two landmarks were indicated as ground truths.

The two convolutional neural networks may be both trained based on a heat map regression.

The first neural network 40 can comprise a residual Unet, and the second network can comprise a residual Unet.

The method discussed above can successfully track the landmarks such as the mitral valve annulus with a mean error in the range of the data resolution. The extraction of the motion parameters of interest is successful, and showed good agreement with the ground truth data based on the Bland-Altmann analysis. The heat map regression avoids the need to learn the highly non-linear domain transfer from pixel to coordinate space, which might explain the high accuracy even though a comparatively small training data set of 83 data sets was used.

The various components described herein may be referred to as "modules" or "units." As noted above, such components may be implemented via any suitable combination of hardware and/or software components as applicable and/or known to achieve the intended respective functionality. This may include mechanical and/or electrical components, FPGAs, processors, processing circuitry, or other suitable hardware components configured to execute instructions or computer programs that are stored on a suitable computer readable medium. Regardless of the particular implementation, such modules and units, as applicable and relevant, may alternatively be referred to herein as "circuitry," "processors," or "processing circuitry."

What is claimed is:

1. A method for determining a motion parameter of a heart, comprising:
   determining a sequence of cardiac magnetic resonance (MR) images showing a time resolved motion of the heart,
   applying a subset of the sequence of cardiac MR images at a first input of a first trained convolutional neural network that is configured to determine, as a first output, a probability distribution of at least two anatomical landmarks in the subset,
   cropping and aligning the sequence of cardiac MR images based on the at least two anatomical landmarks to determine a reframed and aligned sequence of further cardiac MR images,
   wherein each one of the sequence of further cardiac MR images depicts the same orientation of the heart;
   applying the sequence of further cardiac MR images at a second input of a second trained convolutional neural network that is configured to determine, as a second output, a further probability distribution of the at least two anatomical landmarks in each one of the sequence of further cardiac MR images; and
   determining the motion parameter of the heart based on the second output.

2. The method according to claim 1, wherein the subset of the sequence of cardiac MR images comprises a single MR image having a first timeframe in the sequence of cardiac MR images, and
   wherein the first trained convolutional neural network comprises a two-dimensional (2D) convolutional neural network.

3. The method according to claim 1, wherein the second trained convolutional neural network comprises a three-dimensional (3D) convolutional neural network.

4. The method according to claim 1, wherein the motion parameter includes at least one of the following:
   a plane displacement of a mitral valve annulus,
   a plane velocity of the mitral valve annulus,
   a total motion of the mitral valve annulus,
   a septal or a lateral velocity of the mitral valve annulus,
   an evolution of a diameter of the mitral valve annulus,
   a mitral annular tissue velocity,
   a time resolved atrioventricular plane velocity identified with an early diastolic phase of the heart, or
   an end-systolic long axis mitral annular diameter.

5. The method according to claim 1, further comprising:
   performing a pixel space interpolation on the sequence of further cardiac MR images prior to applying the sequence of further cardiac MR images to the second trained convolutional neural network.

6. The method according to claim 1, further comprising:
   fitting, for each of the at least two anatomical landmarks, a predefined distribution to the further probability distribution; and
   taking a maximum of the predefined distribution as a final position of the at least two anatomical landmarks used to determine the motion parameter.

7. The method according to claim 1, further comprising:
   repeating the method with two sequences of MR images having different slice orientations to determine a probability distribution of at least four anatomical landmarks, wherein the motion parameter is determined based on the at least four anatomical landmarks.

8. The method according to claim 1, wherein each one of the first trained convolutional neural network and the second trained convolutional neural network is trained with the same training data set in which the at least two anatomical landmarks were indicated as ground truth.

9. The method according to claim 1, wherein each one of the first trained convolutional neural network and the second trained convolutional neural network is trained based on a heatmap regression.

10. The method according to claim 1, wherein the first trained convolutional neural network and the second trained convolutional neural network each comprises a residual Unet.

11. The method according to claim 1, further comprising:
fitting, for each of the at least two anatomical landmarks, a predefined distribution to the further probability distribution; and
determining the motion parameter based on the predefined distribution as a final position of the at least two anatomical landmarks.

12. The method according to claim 1, further comprising:
repeating the method with two sequences of MR images having different slice orientations to determine a probability distribution of at least four anatomical landmarks.

13. The method according to claim 1, wherein the least two anatomical landmarks in the subset of the sequence of cardiac MR images are from among at least four anatomical landmarks, and further comprising:
determining the motion parameter based on the at least four anatomical landmarks.

14. The method according to claim 1, wherein the probability distribution of the at least two anatomical landmarks in the subset of the sequence of cardiac MR images that is provided as the first output via the first trained convolutional neural network comprises a heatmap distribution that includes the at least two anatomical landmarks.

15. The method according to claim 1, wherein the least two anatomical landmarks in the subset of the sequence of cardiac MR images are identified with respective coordinates of anatomical structures of the heart.

16. The method according to claim 15, further comprising:
fitting, for each of the at least two anatomical landmarks, a predefined distribution to the further probability distribution to refine the coordinates of the at least two anatomical landmarks.

17. A controller configured to determine a motion parameter of a heart, the controller comprising:
a first trained convolutional neural network configured to:
receive a sequence of cardiac MR images showing a time resolved motion of the heart;
apply a subset of the sequence of cardiac MR images as a first input to determine, as a first output, a probability distribution of at least two anatomical landmarks in the subset;
one or more processors configured to perform image processing to crop and align the sequence of cardiac MR images based on the at least two anatomical landmarks to determine a reframed and aligned sequence of further cardiac MR images, each one of the sequence of further cardiac MR images depicting the same orientation of the heart; and
a second trained convolutional neural network configured to:
apply the sequence of further cardiac MR images as a second input to determine, as a second output, a further probability distribution of the at least two anatomical landmarks in each one of the sequence of further cardiac MR images; and
determine the motion parameter of the heart based on the second output.

18. A non-transitory computer-readable storage medium having instructions stored thereon that, when executed by one or more processors of a magnetic resonance (MR) imaging system, cause the MR system to determine a motion parameter of a heart by:
determining a sequence of cardiac magnetic resonance (MR) images showing a time resolved motion of the heart,
applying a subset of the sequence of cardiac MR images at a first input of a first trained convolutional neural network that is configured to determine, as a first output, a probability distribution of at least two anatomical landmarks in the subset,
cropping and aligning the sequence of cardiac MR images based on the at least two anatomical landmarks to determine a reframed and aligned sequence of further cardiac MR images, wherein each one of the sequence of further cardiac MR images depicts the same orientation of the heart;
applying the sequence of further cardiac MR images at a second input of a second trained convolutional neural network that is configured to determine, as a second output, a further probability distribution of the at least two anatomical landmarks in each one of the sequence of further cardiac MR images; and
determining the motion parameter of the heart based on the second output.

* * * * *